United States Patent
Fernandez Prieto et al.

(10) Patent No.: US 11,173,224 B2
(45) Date of Patent: Nov. 16, 2021

(54) GELS COMPRISING A HYDROPHOBIC MATERIAL

(71) Applicant: P&G International Operations SA, Cincinnati, OH (US)

(72) Inventors: Susana Fernandez Prieto, Brussels (BE); Jose Maria Franco, Seville (ES); Emiliano Fratini, Sesto (IT); Craig James, Weston-Super Mare (IT); Inmaculada Martinez Garcia, Huelva (ES); Denis Gerard O'Sullivan, Brussels (BE); Gaurav Saini, Singapore (SG); Harshal Diliprao Santan, Huelva (ES); Johan Smets, Lubbeek (BE); Rahul Vyas, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 162 days.

(21) Appl. No.: 16/029,736

(22) Filed: Jul. 9, 2018

(65) Prior Publication Data

US 2019/0022264 A1    Jan. 24, 2019

(30) Foreign Application Priority Data

Jul. 21, 2017  (EP) .................................. 17382485

(51) Int. Cl.
| | | |
|---|---|---|
| *A61L 9/012* | (2006.01) | |
| *C11D 3/37* | (2006.01) | |
| *C11D 3/50* | (2006.01) | |
| *A61K 8/04* | (2006.01) | |
| *A61K 8/34* | (2006.01) | |
| *A61Q 13/00* | (2006.01) | |
| *C08L 75/06* | (2006.01) | |
| *C08G 18/42* | (2006.01) | |
| *C08G 18/73* | (2006.01) | |
| *C08J 3/24* | (2006.01) | |
| *C08K 5/00* | (2006.01) | |
| *C08J 3/075* | (2006.01) | |
| *C09J 7/10* | (2018.01) | |

(52) U.S. Cl.
CPC .............. *A61L 9/012* (2013.01); *A61K 8/042* (2013.01); *A61K 8/345* (2013.01); *A61Q 13/00* (2013.01); *C08G 18/42* (2013.01); *C08G 18/73* (2013.01); *C08J 3/075* (2013.01); *C08J 3/24* (2013.01); *C08K 5/00* (2013.01); *C08L 75/06* (2013.01); *C09J 7/10* (2018.01); *C11D 3/3715* (2013.01); *C11D 3/502* (2013.01); *C11D 3/505* (2013.01); *C08J 2375/06* (2013.01); *C08K 2201/007* (2013.01)

(58) Field of Classification Search
CPC ......... A61L 9/012; A61Q 13/00; A61K 8/345; A61K 8/042; C11D 3/502; C11D 3/505; C11D 3/3715; C08L 75/06; C08K 5/00; C08K 2201/007; C08G 18/42; C08G 18/73; C08J 3/075; C08J 3/24; C08J 2375/06; C09J 7/10

See application file for complete search history.

(56) References Cited

U.S. PATENT DOCUMENTS

| | | | |
|---|---|---|---|
| 4,466,936 A | 8/1984 | Schapel | |
| 6,130,309 A * | 10/2000 | Reich ....................... | A61K 8/87 424/401 |
| 2010/0184635 A1 | 7/2010 | Tollington et al. | |
| 2011/0015421 A1 | 1/2011 | Abe et al. | |
| 2011/0097289 A1* | 4/2011 | Viala ....................... | A61Q 1/02 424/63 |
| 2018/0208720 A1 | 7/2018 | Hasegawa et al. | |

FOREIGN PATENT DOCUMENTS

| | | |
|---|---|---|
| GB | 965474 A | 7/1964 |
| GB | 1072956 A | 6/1967 |
| JP | S55174748 U | 12/1980 |
| JP | 2006265558 A | 10/2006 |
| WO | WO2016102345 A1 | 6/2016 |

OTHER PUBLICATIONS

Da Silva et al.; Determination of Castor Oil Molecular Weight by Vapour Pressure Osmometry Technique; Laboratory of Separation Process Development, School of Chemical Engineering, State University of Campinas, Zip Code 13081-970, Campinas, SP, Brazil (Year: 2011).*
EP Search Report; 17382485.5-1104; 8 Pages; dated Jan. 26, 2018.
EP Search Report; 17382484.8-1104; 7 Pages; dated Jan. 18, 2018.
U.S. Appl. No. 16/029,741, filed Jul. 9, 2018, Fernandez Prieto, et al.
Pierre Furtwengler and Luc Avérous, Renewable polyols for advanced polyurethane foams from diverse biomass resources, The Royal Society of Chemistry 2018-Polym Chem., 2018, 9,4258-4287.
Desmodur@ eco N 7300, Desmodur® Product Datasheet, Edition Mar. 20, 2017, pp. 1-4.

* cited by examiner

Primary Examiner — Rabon A Sergent
(74) Attorney, Agent, or Firm — Abbey A. Lopez

(57) ABSTRACT

The gel compositions as described herein, are less affected by changes in humidity, are readily formed into complex shapes, and can contain high loadings of the hydrophobic material, even when the material is not highly hydrophobic, and provide a more controlled release of the hydrophobic material. It is believed that the slow release is achieved by forming the gel to have a tight cross-linked network with small pore-size. The pore size is correlated to the average correlation length as measured using Small Angle X-Ray Scattering (SAXS). By limiting the average correlation length to less than 8 nm, preferably from 0.3 nm to 8 nm, more preferably from 0.3 nm to 4 nm, a long lasting release of the hydrophobic material is achieved, rather than a blooming effect, whereby the hydrophobic material is released in a short burst.

15 Claims, No Drawings

GELS COMPRISING A HYDROPHOBIC MATERIAL

FIELD OF THE INVENTION

Gels comprising a hydrophobic material, especially a perfume, for use as air fresheners, in consumer products, and the like.

BACKGROUND OF THE INVENTION

It is desirable to load hydrophobic materials, such as perfumes, into gels. An example of such gels are air freshener gels. Air freshener gels typically comprise a gel, having colloidal dispersions of the perfume distributed within the gel. Generally, it is desired that the hydrophobic material is released slowly over an extended time. For instance, for gels which comprise perfume, if the perfume is released too quickly, the odour can be over-powering and the freshness longevity can be much less than desired.

The gel can be a hydrogel, comprising carrageenan, alginate, carboxymethylcellulose (CMC), gelatin or gellan gum, or the like. Such gels typically require that the perfume is stabilised by the addition of a surface active agent. In addition, such gels are difficult to formulate with high perfume loadings. Where transparent gels are desired, typically even lower perfume loadings are achievable and high levels of the surface active agent are required. Moreover, such gels are sensitive to the ambient humidity.

Anhydrous perfume gels are also known. For instance, U.S. Pat. No. 5,780,527 describes an anhydrous gel element formed by reacting, in the presence of a perfume base, a liquid polymeric material with a cross-linking agent. The rigid, dry and transparent gel element that is thus formed can contain a large proportion of perfume base, of up to 90% w/w based on the total composition. However, such gels are typically highly hydrophobic and are challenging to formulate with perfumes which comprise perfume raw materials which do not have a very high log P.

An additional challenge when making gels comprising hydrophobic materials is syneresis, especially where the hydrophobic material is liquid at ambient temperatures. Syneresis is the expulsion of a liquid from a gel, and can result in a liquid layer of the hydrophobic material on the gel. For complex blends of hydrophobic materials, such as those typically found in perfumes, the individual components of the blend of hydrophobic materials can "weep" out of the gel at different rates. As a result, syneresis can result in a changing odour profile with time from the perfume loaded gel.

In addition, perfume loaded gels are typically challenging to form into complex shapes, since they have to be removable from the forming moulds.

Hence, a need remains for gels comprising hydrophobic material, which are less affected by changes in humidity, are readily formed into complex shapes, and in which high loadings of the hydrophobic material can be achieved, even when the material is not highly hydrophobic, and which provide a more controlled release of the hydrophobic material. Furthermore, a need remains for such gels to be transparent, while also having high perfume loadings.

WO 2003074095 A1 relates to gels comprising from 3 to 80% w/w of perfume base, wherein the gel element comprises a substantially anhydrous thermally reversible gel, as well as articles utilizing such gels. US 20100310492 A1 relates to transparent anhydrous gel comprising volatile substance(s), in particular perfume and non-volatile substance(s), in particular cross-linked silicone network, and not comprising filler or reinforcing agent. WO2013030153 A1 relates to a gel device which allows for prolonged evaporation of an active volatile ingredient contained therein, the gel device comprising an active volatile and a gelling agent essentially formed of carrageenan, further comprising dibutyl lauroyl glutamide and/or dibutyl ethylhexanoyl glutamide, together with a polyol. US 2013/0157922 A1 relates to a water-based carrageenan gel composition that exhibits resistance against syneresis and mottling, by the addition of nonionic cellulose derivatives such as methyl hydroxyethyl cellulose. US 2012/0230936 A1 relates to a solid and self-standing carrageenan gel air freshener composition that exhibits slowed evaporation and extended length-of-life made possible by the addition of relatively small amounts of extenders consisting of C14-C18 fatty alcohols. WO 2012/041411 A1 relates to the use of a mixture of alkoxylated partial fatty acid esters of glycerol, and alkoxylated glycerols, in air freshener gels to reduce the evaporation rate of volatile perfumes and enhance the lifetime of the gels. US 2013/0202788 A1 relates to a nonaqueous self-standing rigid fragrance gel comprising fragrance oil and a hydroxylalkyl cellulose derivative. US2016/0310623 A1 relates to decorative gels, and to candles, air fresheners and other items that use the decorative gels for visual effect. WO2016/173892 A1 relates to a two-stage method for producing a polyurethane hot-melt adhesive, having the stages of A) reacting at least one polyol with at least one diisocyanate, the NCO/OH ratio being greater than 1.5, in order to obtain a reaction mixture containing an isocyanate-functional polyurethane prepolymer and non-converted diisocyanate and B) reacting the reaction mixture obtained in stage A), said mixture containing the isocyanate-functional polyurethane prepolymer and non-converted diisocyanate, with at least one polyester polyol, the NCO/OH ratio being greater than 3. WO 2012088758 A1 relates to an inorganic gel composition for air freshening or disinfecting, comprising a silicon alkoxide or colloidal silica, a volatile or gaseous fragrance and/or disinfectant, water, an acid or base catalyst, a water-soluble solvent, and optionally other volatile components and additives, and a method for preparing the same.

SUMMARY OF THE INVENTION

The present invention relates to a chemically cross-linked gel composition, comprising a hydrophobic material, wherein the gel has an average correlation length of less than 8 nm as measured using Small Angle X-Ray Scattering (SAXS).

DETAILED DESCRIPTION OF THE INVENTION

The gel compositions of the present invention contain a hydrophobic material in their porous structure. The gel compositions of the present invention provide slow release of the hydrophobic material contained therein. It is believed that the slow release is achieved by forming the gel to have a tight cross-linked network having a correlation length of less than 8 nm. Such a correlation length results in a small effective pore-size for the gel. The pore size is correlated to the average correlation length as measured using Small Angle X-Ray Scattering (SAXS). By limiting the average correlation length to less than 8 nm, preferably from 0.3 nm to 8 nm, more preferably from 0.3 nm to 4 nm, a long lasting release of the hydrophobic material is achieved, rather than a blooming effect, whereby the hydrophobic material is released in a short burst.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

All measurements are performed at 25° C. unless otherwise specified.

As used herein, the articles including "a" and "an" when used in a claim, are understood to mean one or more of what is claimed or described.

Gel Composition:

Suitable gel compositions are chemically cross-linked, and have an average correlation length of less than 8 nm as measured using Small Angle X-Ray Scattering (SAXS). However, the gel compositions, described herein, can be formulated to have any desired correlation length.

The gel composition can be formed using a cross-linking agent which forms covalent bonds which are stable mechanically and thermally, so once formed are difficult to break. In contrast, physical cross-links rely on changes in the microstructure to achieve stability, such as crystalline regions or regions of high entanglement.

While physical gels can also hold high levels of hydrophobic material such as perfume, the processing of such physical gels is more delicate, as they are more readily broken during manipulation. In addition, such physical gels typically exhibit larger reductions in volume as the hydrophobic material evaporates, in comparison to the cross-linked gels of the present invention, typically at the level of from 50% to 90% by surface area reduction as the hydrophobic material evaporates. As a result, such physical gels have an extremely non-uniform release profile of the hydrophobic material. In contrast, the cross-linked gels of the present invention exhibit less shrinkage as the hydrophobic material is released, typically of the order of from 10% to 30% by surface area. As a result, the gels of the present invention exhibit a far more uniform release profile of the hydrophobic material.

The gel composition can have an elastic modulus G' of above 0.1 kPa, preferably above 1 kPa, even more preferably above 2 kPa, and below 100 kPa.

The gel can be a chemically cross-linked polyol or derivative thereof. Suitable polyols or derivatives thereof can be selected from the group consisting of: polyol, polyester polyol, polyglycerol and mixtures thereof. Polyols, polyester polyols and polyglycerols comprise multiple hydroxyl groups, and are suitable for forming gels having a compact network. In addition, the resultant gel has greater affinity for hydrophobic materials which are less strongly hydrophobic. Suitable polyols or derivatives thereof can have a molecular weight of from 60 Da to 10000 Da, preferably from 150 Da to 3000 Da, even more preferably from 500 Da to 2000 Da, even more preferably 600 Da to 1300 Da. Longer polyols and derivatives thereof, result in greater flexibility of the gel.

Suitable polyols and derivatives thereof do not comprise terminal hydroxyl groups. Secondary alcohols are particularly suitable. Primary alcohols, having terminal hydroxyl groups, typically result in more linear chains and a more compact network. A combination of primary and secondary alcohols are preferred, since they result in a more desired correlation length. A gel with more optimal pore size is achieved when secondary alcohols are used. Lightly branched polyols and derivatives thereof, such as poly (diethyleneglycol adipates) result in more flexible gels. Preferred polyols and derivatives thereof have at least 2 hydroxyl groups per molecule, more preferably at least 3 hydroxyl groups per molecule.

A polyol is a compound containing multiple hydroxyl groups. Diol polyols, having two hydroxyl-functional groups, result after cross-linking in linear polymers or more open networks having large pore size. In contrast, hydroxyl-functional monomers with functionality larger than two form more compact gels with smaller pore sizes. Suitable polyols include: ethylene glycol, propylene glycol, 1,4-butanediol, 1,6-hexanediol, pentaerythritol, 1,2,6-hexanetriol, 4,6-di-tert-butylbenzene-1,2,3-triol, propanetriol (glycerol), 1,2,5-hexanetriol, 1,2,4-cyclohexanetriol, 2,5-dimethylhexane-1,2,6-triol, 3-hydroxymethylpentane-1,2,5-triol, 1,3,6-hexanetriol, 1,1,5,5-pentanetretraol, 1,2,5,6-hexanetretraol, 1,2,3,4,5,6-hexanehexol (sorbitol) and mixtures thereof.

Polyester polyols are hydroxyl-containing esters. Suitable polyester polyols can be selected from the group consisting of: aliphatic polyester polyols, aromatic polyester polyols, organic oil based polyester polyols, and mixtures thereof. Organic oil based polyester polyols are preferred. Preferred organic oils are vegetable oils since they typically comprise high levels of unsaturation (C=C bonds) and naturally comprise hydroxyl groups. Suitable polyester polyols include: hexanoic acid, 4-hydroxy-, 1,1',1"-(1,2,3-propanetriyl) ester; pentanoic acid, 5-amino-4-hydroxy-, 1,1',1"-(1,2,3-propanetriyl) ester; Polycaprolactone triol; castor oil, hydroxyl sunflower oil (HSO) and mixtures thereof.

Castor oil is particularly suitable. Castor oil (*Ricinus* oil) is a pale yellow and viscous liquid, derived from the bean of the castor plant (*Ricinus communis*). Castor oil is predominately made up of triglycerides of fatty acids that contain 87-90% of ricinoleic acid (cis-12-hydroxyoctadec-9-enoic acid), and can be achieved in high purity grades. Castor oil and its derivatives have been used as polyols for polyurethanes and adhesives. The castor oil can be partially hydrogenated. It has been found that castor oil provides the length of the branches and the position of the hydroxyl groups which is particularly suited for providing a chemically cross-linked gel having a pore size which results in slow release of the hydrophobic material, particularly where the hydrophobic material is a perfume. In addition, the chemically cross-linked gels derived from castor oil show less syneresis of the hydrophobic material from the gel.

Polyglycerols are hydroxy-containing ethers. Polyglycerols are typically obtained by the polymerisation of alkylene oxides (such as epoxides). Suitable alkylene oxides include ethylene oxide, propylene oxide, butylene oxide, and mixtures thereof, using chain initiators such as ethylene glycol, propylene glycol, diethyelene glycol, dipropylene glycol, 1,4-butanediol, neopentyl glycol, pentaerythritol, hexanetriol, sorbitol, glycerol, and mixtures thereof. Suitable polyglycerols can be selected from the group consisting of: α,α-diglycerol, α,β-diglycerol, hyperbranched polyglycerol, dendritic polyglycerol, and mixtures thereof. Hyperbranched polyglycerols are aliphatic polyethers with multiple hydroxyl end groups that are obtained from the nonsymmetric polyaddition of glycidol to glycerol resulting in a globular branch-on-branch structure which provides special internal flexibility. Dendritic polyglycerols are a hyperbranched polyglycerol with a well-defined symmetric and spherical three-dimensional structure around a core. Apart from improving gel elasticity, the dendritic structure with sterically shielded core together with the exceptionally high number of functional groups of hyperbranched polyglycerols produces flexible gels with relatively low pore size, which increase the longevity of final composition by reducing the diffusion rate not only as a consequence of physically entrapping the hydrophobic material, but also enhancing H-bonding and Van der Waals interactions. Such polyglycerols can be purchased from Nanopartica GmbH (Germany) and Sigma-Aldrich. Suitable polyglycerols include: polyethylene glycol, polypropylene glycol, poly (diethylene glycol), poly(dipropylene glycol), poly(1,4-butanediol), poly(neopentyl glycol), poly(1,6-hexanediol), and mixtures thereof. The polyglycerol preferably has from 2 to 50, preferably from 4 to 30 repeat units.

Any suitable cross-linking agent can be used, though cross-linking agents selected from the group consisting of: isocyanates, isothiocynates and mixtures thereof, are preferred. The cross-linking agent can be a linear, branched, or cyclic isocyanate, and mixtures thereof. Cyclic isocyanates and mixtures thereof are preferred. Suitable cyclic isocyanates include heterocyclic isocyanates such as 1,3,5-tris(5-isocyanatopentyl)-1,3,5-triazine-2,4,6(1H,3H,5H)-trione.

Suitable cross-linking agents can be selected from the group consisting of: 1,4-butane diisocyanate (BDI), 1,6 hexamethylene diisocyanate (HMDI), L-Lysine ethyl ester diisocyanate (LDI), 4,4'-Methylenebis(cyclohexyl isocyanate) (H12MDI), Glycolide-ethylene glycol-glycolide isocyanate (Bezwada, LLC), 4,4'-Methylenebis(phenyl isocyanate) (MDI), 2,4'-Methylenebis(phenyl isocyanate) (MDI), 2,2'-Methylenebis(phenyl isocyanate) (MDI), Isophorone diisocyanate (IPDI), 2,4-toluene diisocyanate (2,4-TDI), 2,6-toluene diisocyanate (2,6-TDI), Poly (hexamethylene diisocyanate) (PDI), 1,3-bis(2-isocyanatopropan-2-yl)benzene, Poly (pentamethylene diisocyanate) and mixtures thereof, preferably 1,6 hexamethylene diisocyanate (HMDI), L-Lysine ethyl ester diisocyanate (LDI), Poly (pentamethylene diisocyanate), Poly (hexamethylene diisocyanate) (PDI), 1,3,5-tris(5-isocyanatopentyl)-1,3,5-triazine-2,4,6(1H,3H,5H)-trione, and mixtures thereof. Such cross-linking agents are available from Sigma-Aldrich and from Covestro under trade name of Desmodur® eco N 7300.

The cross-linking agent can have a viscosity below 2.500 mPa·s at 25° C. and an isocyanate equivalent weight of from 15% to 40%, preferably from 18% to 30%. Such cross linking agents are more easily blended with the polyol. As a result, more uniform gels can be achieved.

The gel can be formed using a molar ratio of polyol (or derivative thereof) to cross-linking agent of from 1:0.75 to 1:2, preferably from 1:0.8 to 1:1.6, more preferably from 1:0.8 to 1:1.2. Such ratios of polyol to cross-linking agent typically result in gels having an elastic modulus G' which is of the same order as the viscous modulus G. In addition, ratios of polyol to cross-linking agent typically result in gels having an elastic modulus G' of above 0.1 kPa, preferably above 1 kPa, even more preferably above 2 kPa, and below 100 kPa.

The gel is preferably essentially free, or free of unreacted isocyanates and/or isothiocyanates.

The gel can further comprise a hydroxyl containing polymer, a hydroxyl containing oligomer or mixtures thereof. The hydroxyl containing polymer and/or oligomer can be used to alter the elasticity of the gel composition, and therefore the longevity of the perfume release. since a higher elastic modulus G' slows the perfume release.

Suitable hydroxyl containing polymers can be selected from the group consisting of: poloxamers, gelatins, carrageenan, chitin, chitosan, and mixtures thereof.

Poloxamers are nonionic triblock copolymers composed of a central hydrophobic chain of polyoxypropylene (poly (propylene oxide)) flanked by two hydrophilic chains of polyoxyethylene (poly(ethylene oxide)). Suitable poloxamers have a weight average molecular weight of from 1500 g/mol to 15000 g/mol and a poly(ethylene oxide) weight percentage of from 10% to 80%, preferably from 50% to 80%. Suitable poloxamers are commercially available under the tradename of Pluronic® from BASF.

Gelatins are typically translucent, colorless, and typically obtained from collagen from various animal body parts. They are commonly used as a gelling agent in food, pharmaceutical industry, vitamin capsules, photography, and cosmetic manufacturing. Suitable gelatines can have a bloom of from 90 to 300. Bloom is a test to measure the strength of a gel or gelatin, and is measured according to the method outlined by Bloom in U.S. Pat. No. 1,540,979. The test determines the weight in grams needed by a plunger with a diameter of 0.5 inch (12.7 mm) to depress the surface of the gel 4 mm without breaking it, at a temperature of 25° C. The result is expressed in Bloom (grades). It is usually between 30 and 300 Bloom. To perform the Bloom test on gelatin, a 6.67% by weight gelatin solution is kept for 17-18 hours at 10° C. prior to being tested.

Carrageenan are sulfated polysaccharide for instance derived from red algae, commonly known as Irish moss. They are typically composed principally of alpha-D-galactopyranose-4-sulfate units and 3,6-anhydro-alpha-D-galactopyranose units. At least three forms are known, designated, respectively, as "iota", "kappa" and "lambda" carrageenan which differ in the ratios of the two galactopyranose units and accordingly in their sulfate ester content.

Kappa-carrageenan is the principal component in aqueous extracts from *Chondrus crispus* and *Gigartina stellata*. It is lower in sulfate ester content than iota and lambda carrageenan. Chitosan is typically obtained by deacetylation under alkaline conditions of chitin, which is the second most abundant biopolymer in nature, after cellulose. Chitin can be found as an important constituent of the exoskeleton in animals, especially in crustaceans, molluscs and insects, and it is also the principal polymer in the cell wall of certain fungi. Chitin and chitosan are linear polysaccharides composed of randomly distributed β-(1-4)-linked D-glucosamine (deacetylated unit) and N-acetyl-D-glucosamine (acetylated unit). Chitosan has two types of reactive groups that can be grafted: the free amine groups on the deacetylated units and the hydroxyl groups on the C3 and C6 carbons on acetylated or deacetylated units.

The chitosan of the present invention may have a molecular weight from 10,000 g/mol to 4,000,000 g/mol, preferably from 70,000 g/mol to 1,600,000 g/mol. Suitable chitosan may have a degree of de-acetylation of at least 50%, preferably at least 60%, more preferably at least 70%, even more preferably at least 75%.

The gel can be transparent or even translucent. The gel composition can have any suitable shape, such as star, circular or pyramidal. The gel compositions of the present invention can be moulded or even 3D printed to the desired shape.

The gel composition can be any suitable shape or size, since both define the surface area of the gel composition. It is known that the shape and size of the gel composition can affect the release and longevity of the hydrophobic material. For instance, thin sheets result in faster release and lower longevity than spheres of the same mass of the gel composition. Suitable gel compositions can have a surface area of less than 150 cm$^2$, preferably from 3.0 to 100 cm$^2$, more preferably from 6.0 to 60 cm$^2$.

The surface area can be measured by creating a 3D model of the gel composition using CAD software, and using the CAD software to calculate the surface area. Any suitable CAD software can be used, such as AutoCad® 2013.

Hydrophobic Material:

The gel comprises a hydrophobic material. Suitable hydrophobic material can be present at a level of from 3 wt % to 85 wt %, preferably from 15 wt % to 75 wt %, even more preferably 25 wt % to 70 wt % of the gel composition.

The gel compositions of the present invention can comprise higher levels of hydrophobic material than prior art gels, especially for hydrophobic materials having a log P below 5, and provide improved transparency. Moreover, the perfume release can be controlled by controlling the correlation length of the gel.

Suitable hydrophobic material include a perfume mixture, insect repellent, functional perfume components (FPCs), an aesthetic, a bioactive, a malodor counteractant, and mixtures thereof.

The hydrophobic material can have a log P of more than 0.01, preferably from 0.01 to 6.5, more preferably from 0.5 to 5.5.

Suitable hydrophobic materials can have a log P of greater than 3.0, preferably from 3.0 to 6.5, more preferably from 3.5 to 5.5. Such hydrophobic materials give rise to gels having improved transparency, in addition to faster curing times.

Unlike gels of the prior art, the cross-linked gels of the present invention can incorporate even hydrophobic materials having very low log P. As such, the hydrophobic material can have a log P of less than 3, preferably from 0.01 to 3, even more preferably from 0.5 to 2.8. When attempting to incorporate such low log P hydrophobic material into gels of the prior art, especially physically cross-linked gels of the prior art, the low log P material tends to bleed out of the gel via syneresis. The hydrophobic material can be a blend of hydrophobic material. In such cases, the log P is the weighted average log P of the blend of hydrophobic material. Particularly suitable hydrophobic materials are perfume raw materials, especially perfume mixtures.

Suitable perfume mixtures comprise at least one perfume raw material (PRM). Various PRMs may be used. The perfume mixture can comprise one or more of the PRMs. As used herein, a "perfume raw material" refers to one or more of the following ingredients: fragrant essential oils; aroma compounds; pro-perfumes; materials supplied with the fragrant essential oils, aroma compounds, including stabilizers, diluents, processing agents, and contaminants; and any material that commonly accompanies fragrant essential oils, aroma compounds.

The perfume mixture can comprise at least 20%, preferably at least 40%, even more preferably at least 70% by weight of PRMs having a log P equal or greater than 3 based on total perfume mixture weight. The perfume mixture can even comprise only PRMs having a log P equal or greater than 3. Such high log P perfume mixtures result in faster curing times, as well greater transparency.

As mentioned earlier, the cross-linked gels of the present invention are capable of incorporating even low log P hydrophobic material. Hence, suitable perfume mixtures can comprise at least 30%, preferably at least 45%, even more preferably at least 60% or even at least 70% by weight of PRMs having a log P of less than 3 based on total perfume mixture weight. The perfume mixture can even comprise PRMs having a log P of less than 3.

The hydrophobic material is preferably volatile, especially where the hydrophobic material is a perfume or perfume mixture. As such, hydrophobic materials and blends of hydrophobic materials having a boiling point of less than 450° C., preferably from 60° C. to 400° C., more preferably from 75° C. to 380° C.

At least part or all of the hydrophobic material can be non-volatile or of low volatility, having a boiling point of greater 300° C., preferably greater than 350° C. Such non-volatile or low volatility hydrophobic materials can be as eluents for perfumes and perfume mixtures.

The perfume mixture may include one or more PRM comprising ketones. The PRM comprising ketone can comprise any PRMs which contain one or more ketone moieties and which can impart a desirable scent. The perfume mixture may comprise a PRM comprising a ketone moiety selected from the group consisting of iso jasmone, methyl beta naphthyl ketone, musk indanone, Tonalid™ or musk tetralin, alpha-damascone, beta-damascone, delta-damascone, iso-damascone, damascenone, methyl-dihydrojasmonate, menthone, carvone, camphor, fenchone, alpha-ionone, beta-ionone, dihydro-beta-ionone, gamma-methyl ionone, alpha-methyl ionone, n-beta-methyl ionone isomer, Fleuramone™ or 2-heptylcyclopentan-1-one, dihydrojasmone, cis-jasmone, iso-e-Super™ or patchouli ethanone, methyl cedrylketone or methyl cedrylone, acetophenone, methyl-acetophenone, para-methoxy-acetophenone, methyl-beta-naphtyl-ketone, benzyl-acetone, benzophenone, para-hydroxy-phenyl-butanone, celery ketone or Livescone™, 6-isopropyldecahydro-2-naphtone, dimethyl-octenone, Freskomenthe™ or 2-butan-2-ylcyclohexan-1-one, 4-(1-ethoxyvinyl)-3,3,5,5,-tetramethyl-cyclohexanone, methyl-heptenone, 2-(2-(4-methyl-3-cyclohexen-1-yl)propyl)-cyclopentanone, 1-(p-menthen-6(2)-yl)-1-propanone, 4-(4-hydroxy-3-methoxyphenyl)-2-butanone, 2-acetyl-3,3-dimethyl-norbornane, 6,7-dihydro-1,1,2,3,3-pentamethyl-4 (5h)-indanone, 4-Damascol™ or pepper hexanone, Dulcinyl™ or 4-(1,3-benzodioxol-5-yl)butan-2-one, Gelsone™ or ethyl 2-acetyloctanoate, Hexalon™ or allyl alpha ionone, methyl Cyclocitrone™ or 1-(3,5,6-trimethyl-1-cyclohex-3-enyl)ethanone, methyl-lavender-Ketone™ or 3-(hydroxymethyl)nonan-2-one, Orivone™ or 4-(2-methylbutan-2-yl)cyclohexan-1-one, para-tertiary-butyl-cyclohexanone, Verdone™ or 2-tert-butylcyclohexan-1-one, Delphone™ or 2-pentylcyclopentan-1-one, muscone, Neobutenone™ or 1-(5,5-dimethyl-1-cyclohexenyl)pent-4-en-1-one, Plicatone™ or octahydro-7-methyl-1,4-methanonaphthalen-6(2H)-one, Veloutone™ or 2,2,5-trimethyl-5-pentylcyclopentan-1-one, 2,4,4,7-tetramethyl-oct-6-en-3-one, Tetrameran™ or floral undecenone, Hedione™ or methyl dihydrojasmonate, gamma undecalactone, gamma decalactone, gamma octalactone, ethylene brassylate, pentadecanolide, methyl nonyl ketone, cyclopentadecanone, 3,4,5,6-tetrahydropseudoionone, 8-hexadecenolide, dihydrojasmone, 5-cyclohexadecenone, and mixtures thereof.

The perfume mixture may include a mixture of aldehydes that contribute to scent character and neutralize malodors in vapor and/or liquid phase via chemical reactions. Aldehydes that are partially reactive or volatile may be considered a reactive aldehyde as used herein. Reactive aldehydes may react with amine-based odors, following the path of Schiff-base formation. Reactive aldehydes may also react with sulfur-based odors, forming thiol acetals, hemi thiolacetals, and thiol esters in vapor and/or liquid phase. It may be desirable for these vapor and/or liquid phase reactive aldehydes to have virtually no negative impact on the desired perfume character, color or stability of a product.

The perfume mixture may include a mixture of aldehydes that are partially volatile which may be considered a volatile aldehyde as used herein.

Suitable aldehydes which may be used in the perfume mixture include, but are not limited to, Adoxal™ (2,6,10-Trimethyl-9-undecenal), Bourgeonal™ (4-t-butylbenzenepropionaldehyde), Lilestralis 33™ (2-methyl-4-t-butylphenyl)propanal), Cinnamic aldehyde, cinnamaldehyde (phenyl propenal, 3-phenyl-2-propenal), Citral, Neral (dimethyloctadienal, 3,7-dimethyl-2,6-octadien-1-al), Cyclal C™ (2,4-dimethyl-3-cyclohexen-1-carbaldehyde), Florhydral™ (3-(3-Isopropyl-phenyl)-butyraldehyde), Citronellal (3,7-dimethyl 6-octenal), Cymal (2-methyl-3-(para-isopropylphenyl)propionaldehyde), cyclamen aldehyde, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), Helional™ (3-(1,3-Benzodioxol-5-yl)-2-methylpropanal); 2-Methyl-3-(3,4-methylenedioxyphenyl)propanal), Intreleven aldehyde (undec-10-en-1-al), Ligustral™ (2,4-dimethylcyclohex-3-ene-1-carbaldehyde), Trivertal™ (2,4-dimethyl-3-cyclohexene-1-carboxaldehyde), Jasmorange™ or satinaldehyde (2-methyl-3-tolylproionaldehyde, 4-dimethylbenzenepropanal), Lyral™ (4-(4-hydroxy-4-methyl pentyl)-3-cyclohexene-1-carboxaldehyde), Melonal™ (2,6-Dimethyl-5-Heptenal), Methoxy Melonal (6-methoxy-2,6-dimethylheptanal), methoxycinnamaldehyde (trans-4-methoxycinnamaldehyde), Myrac Aldehyde™ (iso hexenyl tetraydrobenzaldehyde), Trifernal™ ((3-methyl-4-phenyl propanal, 3-phenyl butanal), lilial (3)-(4-tert-Butylphenyl)-2methylpropanal), benzenepropanal (4-tert-butyl-alpha-methyl-hydrocinnamaldehyde), Dupical™ (muguet butanal), tricyclodeclyidenebutanal (4-Tricyclo5210-2,6decylidene-8butanal), Melafleur™ (1,2,3,4,5,6,7,8-octahydro-8,8-dimethyl-2-naphthaldehyde), Methyl Octyl Acetaldehyde, aldehyde C-11 MOA (2-methyl deca-1-al), Onicidal™ (2,6,10-trimethyl-5,9-undecadien-1-al), Citronellyl oxyacetaldehyde, Muguet aldehyde 50™ (3,7-dimethyl-6-octenyl) oxyacetaldehyde, phenylacetaldehyde, Mefranal™ (3-methyl-5-phenyl pentanal), dimethyl tetrahydrobenzene aldehyde (2,4-dimethyl-3-cyclohexene-1-carboxaldehyde), 2-phenylproprionaldehyde, Hydrotropaldehyde (2-phenyl propionaldehyde), Canthoxal™ (para-anisyl propanal), anisylpropanal 4-methoxy-alpha-methyl benzenepropanal (2-anisylidene propanal), Cyclemone A™ (1,2,3,4,5,6,7,8-octahydro-8,8-dimethyl-2-naphthaldehyde), and Precyclemone B™ (1-cyclohexene-1-carboxaldehyde).

Still other suitable aldehydes include, but are not limited to, acetaldehyde (ethanal), pentanal, valeraldehyde, amylaldehyde, Scentenal™ (octahydro-5-methoxy-4,7-Methano-1H-indene-2-carboxaldehyde), propionaldehyde (propanal), Cyclocitral, beta-cyclocitral, (2,6,6-trimethyl-1-cyclohexene-1-acetaldehyde), Iso Cyclocitral™ (2,4,6-trimethyl-3-cyclohexene-1-carboxaldehyde), isobutyraldehyde, butyraldehyde, isovaleraldehyde (3-methyl butyraldehyde), methylbutyraldehyde (2-methyl butyraldehyde, 2-methyl butanal), Dihydrocitronellal (3,7-dimethyl octan-1-al), 2-Ethylbutyraldehyde, 3-Methyl-2-butenal, 2-Methylpentanal, 2-Methyl Valeraldehyde, Hexenal (2-hexenal, trans-2-hexenal), Heptanal, Octanal, Nonanal, Decanal, Lauric aldehyde, Tridecanal, 2-Dodecanal, Methylthiobutanal, Pentanedial, Heptenal, cis or trans-Heptenal, Undecenal (2-, 10-), 2,4-octadienal, Nonenal (2-, 6-), Decenal (2-, 4-), 2,4-hexadienal, 2,4-Decadienal, 2,6-Nonadienal, Octenal, 2,6-dimethyl 5-heptenal, 2-isopropyl-5-methyl-2-hexenal, beta methyl Benzenepropanal, 2,6,6-Trimethyl-1-cyclohexene-1-acetaldehyde, phenyl Butenal (2-phenyl-2-butenal), 2-Methyl-3 (p-isopropylphenyl)-propionaldehyde, 3-(p-isopropylphenyl)-propionaldehyde, p-Tolylacetaldehyde (4-methylphenylacetaldehyde), Anisaldehyde (p-methoxybenzene aldehyde), Benzaldehyde, Vernaldehyde™ (1-Methyl-4-(4-methylpentyl)-3-cyclohexenecarbaldehyde), Heliotropin (piperonal) 3,4-Methylene dioxy benzaldehyde, alpha-Amylcinnamic aldehyde, 2-pentyl-3-phenyl-propenoic aldehyde, Vanillin (4-methoxy 3-hydroxy benzaldehyde), Ethyl vanillin (3-ethoxy 4-hydroxybenzaldehyde), Hexyl Cinnamic aldehyde, Jasmonal H™ (alpha-n-hexyl-cinnamaldehyde), Floralozone™ (para-ethyl-alpha, alpha-dimethyl Hydrocinnamaldehyde), Acalea™ (p-methyl-alpha-pentylcinnamaldehyde), methylcinnamaldehyde, alpha-Methylcinnamaldehyde (2-methyl 3-pheny propenal), alpha-hexylcinnamaldehyde (2-hexyl 3-phenyl propenal), Salicylaldehyde (2-hydroxy benzaldehyde), 4-ethyl benzaldehyde, Cuminaldehyde (4-isopropyl benzaldehyde), Ethoxybenzaldehyde, 2,4-dimethylbenzaldehyde, Veratraldehyde (3,4-dimethoxybenzaldehyde), Syringaldehyde (3,5-dimethoxy 4-hydroxybenzaldehyde), Catechaldehyde (3,4-dihydroxybenzaldehyde), Safranal (2,6,6-trimethyl-1,3-diene methanal), Myrtenal (pin-2-ene-1-carbaldehyde), Perillaldehyde (4-prop-1-en-2-ylcyclohexene-1-carbaldehyde), 2,4-Dimethyl-3-cyclohexene carboxaldehyde, 2-Methyl-2-pentenal, 2-methylpentenal, pyruvaldehyde, formyl Tricyclodecan, Mandarin aldehyde, Cyclemax™ (cuminyl acetaldehyde), Pino acetaldehyde, Corps Iris, Maceal (bark carbaldehyde), and Corps 4322.

The perfume mixture may include one or more of the following perfume raw materials: cyclic ethylene dodecanedioate, 4-tertiary butyl cyclohexyl acetate or Vertenex™, allyl amyl glycolate, allyl caproate, allyl cyclohexane propionate, allyl heptanoate, amber xtreme, ambrox, isoamyl acetate, isoamyl propionate, anethole usp, benzyl acetate, benzyl propionate, cis-3-hexen-1-ol, beta naphthol methyl ether or nerolin, caramel furanone, caryophyllene extra, Cinnamalva™ or Cinnamyl Nitrile, cinnamyl acetate, cinnamyl nitrile, cis-3-hexenyl butyrate, cis-3-hexenyl acetate, cis-3-hexenyl alpha methyl butyrate, cis-6-nonen-1-ol, citrathal or citral diethyl acetal, citronellol, citronellyl acetate, citronellyl butyrate, clonal or dodecane nitrile, coranol or 2,2-dimethyl cyclohexanepropanol, coumarin, cumin nitrile, cuminic alcohol, tricyclodecenyl isobutirate or cyclabute, cyclohexyl ethyl acetate, dihydromyrcenol, dimethyl anthranilate, dimethyl benzyl carbinyl acetate, dimethyl-2 6-heptan-2-ol or freesiol, sandal pentenol or ebanol, ethyl-2-methyl pentanoate, ethyl acetoacetate, ethyl linalool, ethyl maltol, ethyl phenyl glycidate, ethyl vanillin, ethyl-2-methyl butyrate, eucalyptol, eugenol, flor acetate, ozone propanal or floralozone, Fructalate™ or raspberry dicarboxylate, geraniol or trans-3,7-dimethyl-2,7-octadien-1-ol, Grisalva™ or amber furan, Habanolide™ or (E)-12-musk decenone, Helvetolide™ or musk propanoate, hexyl acetate, hexyl-2-methyl butyrate, Indocolore™ or 1-phenylvinyl acetate, iso bornyl acetate, iso eugenyl acetate, iso propyl myristate, isoamyl butyrate, isoeugenol, Koumalactone™ or dihydromint lactone, laevo trisandol or sandranol, Lemonile™ or homogeranyl nitrile, Levistamel™ or mesitene lactone, linalool, linalyl acetate, linalyl iso butyrate, lymolene or dihydromyrcenol, menthol, methyl dioxolan or Fructone™, methyl iso butenyl tetrahydro pyran, methyl Pamplemousse™ or grapefruit acetal, methyl phenyl carbinyl acetate or styrallyl acetate, methyl salicylate, Montaverdi™ or green cyclopropionate, Mugetanol™ or muguet ethanol, neocaspirene, neofolione or melon nonenoate nerolidol, orange terpenes, orcinyl-3 or 3-methoxy-5-methylphenol, Oxane™ or cis-*galbanum* oxathiane, para cresyl methyl ether or para methyl anisole, patchouli, phenyl ethyl alcohol, phenyl ethyl dimethyl carbinol, Polysantol™ or santol pentenol, prenyl acetate, Sauvignone™ or 5-mercapto-5-methyl-3-hexanone, Sclareolate™ or clary propionate, shisolia, Strawberiff™ or 2-methyl-2-pentenoic acid, terpinolene or 4-isopropylidene-1-methylcyclohexene, tetrahydro Muguol™ or citrus ocimenol, Thesaron™ (1R,6S)-2,2,6-Trimethyl-cyclohexanecarboxylic acid ethyl ester, Tobacarol™ or 5-tetramethyl oxatricyclododecane, Undecavertol™ or violet decenol, Verdox™ or green acetate, verdural B™ or (Z)-3-hexen-1-yl isobutyrate, Violettyne™ or violet dienyne, Violiff™ or violet methyl carbonate, and mixtures thereof.

The perfume mixture may contain functional perfume components ("FPCs"). FPCs are a class of perfume raw materials with evaporation properties that are similar to traditional organic solvents or volatile organic compounds ("VOCs"). "VOCs", as used herein, means volatile organic compounds that have a vapor pressure of greater than 0.2 mm Hg measured at 20° C. and aid in perfume evaporation. Exemplary VOCs include the following organic solvents: dipropylene glycol methyl ether ("DPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether. VOCs are commonly used at levels greater than 20% in a fluid composition to aid in perfume evaporation.

The FPCs aid in the evaporation of perfume materials and may provide a hedonic, fragrance benefit. FPCs may be used in relatively large concentrations without negatively impacting perfume character of the overall composition. As such, the fluid composition may be substantially free of VOCs, meaning it has no more than 18%, alternatively no more than 6%, alternatively no more than 5%, alternatively no more than 1%, alternatively no more than 0.5%, by weight of the composition, of VOCs. The fluid composition may be free of VOCs.

Perfume materials that are suitable for use as a FPC can also be defined using odor detection threshold ("ODT") and non-polarizing scent character for a given perfume character scent camp.

FPCs may have an ODT from greater than 1.0 parts per billion ("ppb"), alternatively greater than 5.0 ppb, alternatively greater than 10.0 ppb, alternatively greater than 20.0 ppb, alternatively greater than 30.0 ppb, alternatively greater than 0.1 parts per million.

These FPCs can be either an ether, an alcohol, an aldehyde, an acetate, a ketone, or mixtures thereof.

FPCs may be volatile, low boiling point (B.P.) perfume materials. Exemplary FPC include iso-nonyl acetate, dihydro myrcenol (3-methylene-7-methyl octan-7-ol), linalool (3-hydroxy-3, 7-dimethyl-1, 6 octadiene), geraniol (3, 7 dimethyl-2, 6-octadien-1-ol), d-limonene (1-methyl-4-isopropenyl-1-cyclohexene, benzyl acetate, benzyl benzoate, isopropyl mystristate, diethyl phthalate and mixtures thereof.

The total amount of FPCs in the perfume mixture may be greater than 30%, alternatively greater than 50%, alternatively greater than 60%, alternatively greater than 70%, alternatively greater than 80%, alternatively from 30% to 100%, alternatively from 50% to 100%, alternatively from 60% to 100%, alternatively from 70% to 100%, alternatively from 80% to 100%, alternatively from 85% to 100%, alternatively from 90% to 100%, by weight of the perfume mixture. The perfume mixture may consist entirely of FPCs (i.e. 100 wt. %).

Table 1 lists a non-limiting, exemplary fluid composition comprising FPCs and their reported values for B.P.

TABLE 1

| Material Name | wt. % | B.P. (° C.) at 760 mmHg |
|---|---|---|
| Benzyl Acetate (CAS # 140-11-4) | 1.5 | 214 |
| Ethyl-2-methyl Butyrate (CAS # 7452-79-1) | 0.3 | 132 |
| Amyl Acetate (CAS # 628-63-7) | 1.0 | 149 |
| Cis 3 Hexenyl Acetate (CAS # 3681-71-8) | 0.5 | 169 |
| Ligustral (CAS # 27939-60-2) | 0.5 | 177 |
| Melonal (CAS # 106-72-9) | 0.5 | 116 |
| Hexyl Acetate (CAS # 142-92-7) | 2.5 | 146 |
| Dihydro Myrcenol (CAS# 18479-58-8) | 15 | 198 |
| Phenyl Ethyl Alcohol (CAS# 60-12-8) | 8 | 219 |
| Linalool (CAS # 78-70-6) | 25.2 | 205 |
| Geraniol (CAS# 106-24-1) | 5 | 238 |
| Iso Nonyl Acetate (CAS# 40379-24-6) | 22.5 | 225 |
| Benzyl Salicylate (CAS # 118-58-1) | 3 | 320 |
| Coumarin (CAS # 91-64-5) | 1.5 | 267 |
| Methyl Dihydro Jasmonate (CAS# 24851-98-7) | 7 | 314 |
| Hexyl Cinnamic Aldehyde (CAS # 101-86-0) | 6 | 305 |

Preferably, the hydrophobic material is a liquid under ambient conditions (such as from 5° C. to 25° C.).

Suitable malodour counteractants include amine functional polymers, metal ions, cyclodextrins, cyclodextrin derivatives, oxidizing agents, activated carbon, and combinations thereof.

Suitable insect repellents include any typical insect and/or moth repellents such as citronellal, citral, N, N-diethyl-meta-toluamide, Rotundial, 8-acetoxycarvotanacenone, and combinations thereof. Other examples of insect and/or moth repellent for use herein are disclosed in U.S. Pat. Nos. 4,449,987, 4,693,890, 4,696,676, 4,933,371, 5,030,660, 5,196,200, "Semio Activity of Flavour and Fragrance molecules on various Insect Species", B. D. Mookherjee et al., published in Bioactive Volatile Compounds from Plants, ASC Symposium Series 525, R. Teranishi, R. G. Buttery, and H. Sugisawa, 1993, pp. 35-48.

Suitable sensates include menthol (L, D, racemic), eucalyptol and *Eucalyptus* oil, peppermint oils, cornmint or *arvensis* 15 mint oils, spearmint oils, carvone, clove oils, cinnamic aldehyde and cinnamon derivatives, aliphatic carboxamides, ketals, cyclohexyl derivatives, mono-menthyl succinated and mixtures thereof. Some examples are: WS-3 available as ISE 3000 and WS-23 available as ISE 1000 from Qaroma, Inc. MGA available from Symrise, TK10, Coolact available from LIPO Chemicals of Paterson, N.J., and Physcool™.

Suitable aesthetics include colorants such as dyes or pigments and other aesthetic materials which can be added to enhance the appearance of the perfume gel. Non-limiting examples of colorants are Rhodamine, Fluorescein, Phathalocyanine, alumina and mixtures thereof. Non-limiting examples of particles with different shapes and sizes are epoxy coated metalised aluminium polyethylene terephthalate, polyester beads, candelilla beads, silicates and mixtures thereof. Such aesthetic materials are available from Glittergo Limited, Impact colors and CQV Co. Ltd.

Multilayer Gel Composition:

Multilayer gel compositions can enable the introduction of different ingredients in the different layers. For instance, the multilayer gel composition can comprise different hydrophobic material in two or more layers. For instance, the multilayer gel can comprise two or more layers, wherein at least 2 layers have a different hydrophobic material, for instance, two different odour compositions. For such multilayer gels, the odour profile changes as the perfume is released. Multilayer gel compositions can comprise layers having different elasticity and hence, different release rates. As such, the odour profile changes as the perfume is released.

A multilayer gel composition can also be used to provide an improved release profile for the hydrophobic material. In particular, the gel composition can comprise an inner layer and one or more outer layer which fully or partially surrounds the inner layer, wherein the average correlation length of the gel compositions of the layers are different. For instance, the inner layer can have an average correlation length of greater than 1.5 to 8.0 nm, preferably greater than 1.6 to 6.0 nm, and the one or more outer layer can have an average correlation length of from 0.3 to 4.0 nm, preferably 0.5 to 1.5 nm, more preferably 0.5 to 1.0 nm, with the proviso that the average correlation length of the outer layer is less than the average correlation length of the inner layer. Such multilayer compositions enable the hydrophobic material to more rapidly diffuse to the interface between the inner layer and adjacent outer layer, before diffusing through the outer layer in a more controlled manner. This results in a more consistent release of the hydrophobic material, such as perfume, over lifetime of the multilayer gel composition.

One or more layer can comprise different levels of cross-linking agent, in order to provide a different degree of curing. In such multilayer gel compositions, one layer can have a higher tackiness, in order to glue the multilayer gel composition to a surface.

The different layers of the multilayer gel can also comprise different hydrophobic materials or other additives. For instance, a first layer can comprise a perfume composition, a second layer can comprise a malodour component, and an optional third layer can be, or comprise, an adhesive.

The multilayer gel composition comprises at least two layers, or at least three layers. The layers can be lamellar. Alternatively, a second layer can be embedded in a first layer, such as dispersed droplets.

At least one layer preferably comprises a hydrophobic material which is a perfume.

A second layer can be an adhesive layer. When present, the adhesive layer is preferably an outer layer. The adhesive layer can have a G' below 100 Pa, preferably below 60 Pa, even more preferably below 20 Pa. The adhesive layer preferably has a G' of greater than 3 Pa. The adhesive layer preferably has a G" which is greater than the G'.

One or more layers of the multilayer gel composition can comprise a cross-linked polyol or derivative thereof. One or more layers of the multilayer gel composition can comprise a cross-linked polyol or derivative thereof, made by cross-linking the same polyol or derivative thereof.

The gel of the first layer can be formed using a molar ratio of polyol (or derivative thereof) to cross-linking agent of from 1:0.75 to 1:2, preferably from 1:0.8 to 1:1.6, more preferably from 1:0.8 to 1:1.2, and the gel of the second layer can be formed using a molar ratio of polyol (or derivative thereof) to cross-linking agent of from 1:0.05 to 1:0.7, preferably from 1:0.1 to 1:0.6, more preferably from 1:0.15 to 1:0.6.

Not all layers of the multilayer gel composition need to comprise a hydrophobic material.

The multilayer gel composition can comprise a core-shell structure with an outer layer surrounding the inner layer. Alternatively, the multilayer gel composition can comprise an inner layer which is partially surrounded by an outer layer. For instance, the inner layer can be attached to an impermeable layer, such as a plastic moulded item, with an outer layer covering at least part, preferably all of the surface of the inner layer which is not in contact with the impermeable layer. For such items, it is preferable that least 90% of the surface area of the inner layer is surrounded by the impermeable layer or an outer layer of gel composition.

Process of Making:

The polyol or derivative thereof, is mixed with hydrophobic material, and optionally a hydroxyl containing polymer is added. Then, the cross-linking agent is added at a temperature from 5° C. to 35° C., preferably 15° C. to 30° C. and further mixed in order to provide a homogeneous mixture. The mixture is poured into a mould of the desired shape, and cured, preferably at a curing temperature from 20° C. to 30° C. Such temperatures limit the evaporation of volatile components of the hydrophobic material. Alternatively, the mixture can be kept at 5° C. or less, in order to avoid curing. Curing will then start only once the temperature is raised to the curing temperature.

The polyol or derivative thereof can be mixed with the cross-linking agent, and optionally a hydroxyl containing polymer, preferably at a temperature from 20° C. to 85° C., more preferably from 30° C. to 75° C., for 10 min to 10 hours, preferably from 15 min to 2 hours. The mixture is cooled down and the hydrophobic material is added preferably at a temperature from 10° C. to 40° C., more preferably 15° C. to 30° C. and can be further mixed, for instance, from 15 to 120 min. The mixture is poured into the desired mould and cured, preferably at a temperature from 20° C. to 30° C.

Alternatively, all of the components of the gel composition can be blended at a low temperature, such as 5° C. or less, before the temperature is increased to the curing temperature.

In order to provide a multilayer gel composition, a first mixture is prepared following one of the processes described above in order to provide a first gel layer, and before the first gel layer is substantially free of isocyanates, a second mixture is added to form the second gel layer. Additional layers can be added by using the same procedure. In a preferred embodiment, the gel composition comprises at least one adhesive layer which is preferably added as the last layer. If via IR-spectroscopy, a visible peak for the free isocyanate is not seen, a gel composition is considered substantially free of NCO group. The IR-spectra should be taken within 5 minutes of taking the sample of gel-composition.

In order to provide a multilayer gel composition having a core-shell structure, the gel composition can be coated using the following steps
(a) providing a gel structure having an exterior surface; and
(b) applying a coating to the exterior surface to provide the shell.

The coating can be applied by any of the following means:
(a) spraying the coating onto the exterior surface;
(b) dipping the gel structure into a solvent-containing coating composition; or
(c) dipping the gel structure into a solvent-free molten coating composition.

Methods

1) Correlation Length Determination by Small Angle X-Ray Scattering (SAXS):

Sample Preparation:

A small (~1 mm×~1 mm×~3 mm) segment of gel is cut using a scalpel and it is placed into a demountable cell with Kapton film windows giving a sample thickness of 1 mm

SAXS:

SAXS measurements are performed using a HECUS, S3-MICRO Kratky-type camera equipped with a position sensitive, 50M OED detector comprising of 1024 channels, 54 μm in width. An ultra-brilliant point microfocus X-ray source (GENIX-Fox 3D, Xenocs, Grenoble) provides Cu Kα radiation with a wavelength, λ, of 1.542 Å at a maximum power of 50 W. A sample-to-detector distance of 281 mm allows for a measurable q-range between 0.01 and 0.54 Å$^{-1}$ (where q, the scattering vector, is given by q=4π/λ sin θ, and 2θ is the scattering angle). The S3-MICRO camera is calibrated using silver behenate (d=58.38 Å) and kept under vacuum to reduce scattering from air. Measurements are performed at a temperature of 25° C. and controlled by a Peltier element with an accuracy of 0.1° C. Raw scattering data is corrected for the scattering of the cell and unreacted pure castor oil using a relative transmission factor.

Data Analysis:

The intensity of scattered radiation, I(Q), for a typical gel has a Q-dependence following a Lorentzian form (equation 1.0) (Hammouda, B. Insight into Clustering in Poly(ethylene oxide) Solutions. *Macromolecules* 2004. 37, 6932-6937):

$$I(Q) = \frac{I(0)}{1 + (Q\xi)^2} \quad \text{(eq. 1.0)}$$

wherein,

I(Q) is intensity of scattered irradiation

I(0) is the scattering length intensity at q=0

ξ is the correlation length

This describes scattering from a polymer where the polymer chains are considered as a "blob" of size ξ A plot of 1/I(Q) vs. Q$^2$ will yield a straight line in the low q region with a intercept of 1/I(0) and slope of ξ$^2$/I(0) from which the correlation length can be obtained.

2) IR Spectroscopy—NCO Analysis:

Instrument Details:

Attenuated total reflection (ATR) Fourier transformation infrared spectroscopy (FTIR) is used to determine the main functional groups of synthesized adhesives. All the spectra are obtained by the Dilab FTS3500ARX (Varian) apparatus in a wavenumber range of 4000-400 cm$^{-1}$, at 4 cm$^{-1}$ resolution in the transmission mode.

Sample Preparation:

50 mg of the prepared gel (high viscous or adhesive material included) is put into the sample holder of the equipment without any further treatment.

Result:

Polyols and derivatives and thereof show a broad band in the range 3350-3600 cm$^{-1}$ corresponding to hydroxyl groups, moreover, for polyester polyols an intense characteristic peak at 1740 cm$^{-1}$ corresponding to the stretching vibration of C=O carbonyl bond of the polyester part. Typical absorption peak of free isocyanate (—N=C=O) groups are shown at around 2260-2275 cm$^{-1}$, exact wave length depends on the substitution of the adjacent C. If spectra, does not show a visible peak for the free isocyanate it is considered essentially free of NCO group and therefore the sample is fully cured.

3) Percentage NCO Determination:

Equivalent weight (eq. wt.) is used to calculate wt % of isocyanate present in the composition, the reactive group is —N=C=O (NCO). Its concentration is measured by weight percent NCO.

$$\text{Isocyanate equivalent weight (\%)} = \frac{42.02 * n}{\text{Mol. Wt. of isocyanate}} \times 100$$

Where, n is number of isocyanate groups per molecule

4) Method for Determining the Elastic Modulus of a Gel Composition:

Elastic modulus is measured using a controlled stress rheometer (such as an HAAKE MARS from Thermo Scientific, or equivalent), using a 35 mm titanium parallel plate (PP35 Ti) at 25±1° C. The elastic modulus is obtained by small amplitude oscillatory shear stress sweep from 0.01 Pa to 100 Pa at a frequency of 0.5 Hz, taking 25 points logarithmically distributed over the shear stress range. Elastic modulus values at each shear stress are obtained as a mean of 3 oscillatory repetitions. Elastic modulus value is obtained from linear viscoelastic region. The linear viscoelastic region is the shear stress range in which the elastic modulus has a variation lower than 10%.

5) Method of Determining Viscosity of a Cross-Linking Agent:

The viscosity of a cross linking agent composition is determined using a Brookfield ° RVDV-E rotational viscometer, at 60 rpm, at 21° C. Spindle 1 is used for viscosities from 100 mPa·s to 20,000 mPa·s.

6) Method of Determining Log P of the Hydrophobic Material:

The partition coefficient, P, is the ratio of concentrations of a compound in a mixture of two immiscible phases at equilibrium, in this case n-Octanol/Water. The value of the log of the Octanol/Water Partition Coefficient (log P) can be measured experimentally using well known means, such as the "shake-flask" method, measuring the distribution of the solute by UV/VIS spectroscopy (for example, as described in "The Measurement of Partition Coefficients", Molecular Informatics, Volume 7, Issue 3, 1988, Pages 133-144, by Dearden J C, Bresnan). Preferably, the log P is computed for each PRM in the perfume mixture being tested. The log P of an individual PRM is preferably calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

The log P of blends of hydrophobic material is calculated as the weight average of the log P of the individual hydrophobic material in the blend.

7) Odor Detection Threshold (ODT) Determination

ODTs may be determined using a commercial GC equipped with flame ionization and a sniff-port. The GC is calibrated to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and concentration of the material can be calculated. To determine whether a material has a threshold below 50 ppb, solutions are delivered to the sniff port at the back-calculated concentration. A panelist sniffs the GC effluent and identifies the retention time when odor is noticed. The average across all panelists determines the threshold of noticeability. The necessary amount of analyte is injected onto the column to achieve a 50 ppb concentration at the detector. Typical GC parameters for determining ODTs are listed below. The test is conducted according to the guidelines associated with the equipment.

Equipment:
GC: 5890 Series with FID detector (Agilent Technologies, Ind., Palo Alto, Calif., USA);
7673 Autosampler (Agilent Technologies, Ind., Palo Alto, Calif., USA);
Column: DB-1 (Agilent Technologies, Ind., Palo Alto, Calif., USA)
Length 30 meters ID 0.25 mm film thickness 1 micron (a polymer layer on the inner wall of the capillary tubing, which provide selective partitioning for separations to occur).
Method Parameters:
Split Injection: 17/1 split ratio;
Autosampler: 1.13 microliters per injection;
Column Flow: 1.10 mL/minute;
Air Flow: 345 mL/minute;
Inlet Temp. 245° C.;
Detector Temp. 285° C.
Temperature Information:
Initial Temperature: 50° C.;
Rate: 5 C/minute;
Final Temperature: 280° C.;
Final Time: 6 minutes;
Leading assumptions: (i) 12 seconds per sniff
(ii) GC air adds to sample dilution.

EXAMPLES

The following are examples of perfume mixtures of use as hydrophobic materials for gel compositions of the present invention:

| hydrophobic material | Ex-A | Ex-B | Ex-C | Ex-D | Ex-E | Ex-F | Ex-G | Ex-H |
|---|---|---|---|---|---|---|---|---|
| alcohols | 64.35 | 31.88 | 25 | 4.75 | 23 | 28.5 | 38.4 | 9 |
| aldehydes | 4.14 | 6.75 | 14.8 | 13.39 | 12.5 | 23 | 7.19 | 17.01 |
| ketones | 0 | 1.75 | 1.4 | 4.83 | 3.65 | 18 | 22.35 | 4.2 |
| esters | 13.5 | 25.12 | 53.4 | 63.31 | 53.15 | 21.2 | 30.86 | 52.39 |
| ether | 14.71 | 34.5 | 0 | 10.05 | 1.1 | 6.2 | 0 | 13 |
| hydrocarbons | 3.3 | 0 | 4 | 1 | 4 | 0.1 | 1.2 | 4 |
| Nitriles | 0 | 0 | 0.4 | 0.4 | 1.6 | 3 | 0 | 0 |
| others | 0 | 0 | 1 | 2.27 | 1 | 0 | 0 | 0.4 |
| minimum wt % of PRMs with a logP below 1 | 13.9 | 13.25 | | 10 | 1.7 | | | |
| minimum wt % of PRMs with a logP equal or greater than 1 and less than 2 | 4.05 | 39.38 | | 21.24 | 30.5 | 15.5 | 24.1 | 20 |
| minimum wt % of PRMs with a logP equal or greater than 2 and less than 3 | 57.6 | 47.37 | 5 | 10.6 | 26.95 | 29.3 | 25.3 | 19.8 |
| minimum wt % of PRMs with a logP equal or greater than 3 and less than 4 | 24.45 | | 86.4 | 46.28 | 28.75 | 30.2 | 18 | 52.2 |
| minimum wt % of PRMs with a logP equal or above 4 | | | 8.6 | 11.88 | 6.6 | 12.1 | 25 | 8 |

Example 1: Making a Gel Composition Comprising Fragrance and Aesthetics

In a 250 mL round bottom flask, 21 grams of castor oil (94481, Guinama, Spain) and 61 grams of perfume composition HC-D are added and mixed at 300 rpm for 30 minutes using a magnetic stirrer at 25° C. till an homogeneous solution is formed. Then, 18 grams of poly(hexamethylene diisocyanate) (418005, Sigma Aldrich) are added and the mixture is mixed for 30 minutes at 25° C. Then, 0.1 grams sparkling stars and glitters as aesthetics are added and the composition is mixed for 5 minutes. Magnetic bar is removed and the composition is poured into a cube mould and closed to avoid fragrance evaporation during curing. Curing at 25° C. takes 72 hours. Then, the gel composition is taken out of the mould and is ready to be used.

Example 2: Making a Gel Composition Comprising Fragrance

In a 250 mL round bottom flask, 18.9 grams of castor oil (94481, Guinama, Spain) and 65 grams of perfume composition HC-A are added and mixed at 300 rpm for 60 minutes using a magnetic stirrer at 25° C. till a homogeneous solution is formed. Then, 16.1 grams of poly(hexamethylene diisocyanate) (418005, Sigma Aldrich) are added and the mixture is mixed for 30 minutes at 25° C. Magnetic bar is removed and the composition is poured into a cube mould and closed to avoid fragrance evaporation during curing. Curing at 25° C. takes 72 hours. Then, the gel composition is taken out of the mould and is ready to be used.

Example 3: Making a Multilayer Gel Composition Comprising 2 Hydrophobic Compositions and an Adhesive Layer In a 250 mL round bottom flask, 21 grams of castor oil (94481, Guinama, Spain) and 18 grams of Desmodur® eco N 7300 (Covestro Germany) are added and mixed with a magnetic stirrer at 300 rpm for 20 minutes at 75° C. Then mixture is cooled down to 30° C. and 36 grams of perfume composition HC-A and 25 grams isopropyl myristate are added and mixed at 300 rpm for 40 min. Magnetic bar is removed and the composition is poured into a round mould and closed to avoid fragrance evaporation during curing.

After 12 hours, in a 250 mL round bottom flask, 21 grams of castor oil (94481, Guinama, Spain) and 18 grams of Desmodur® eco N 7300 (Covestro Germany) are added and mixed with a magnetic stirrer at 300 rpm for 40 minutes at 75° C. Then mixture is cooled down to 30° C. and 61 grams of perfume composition HC-G are added and mixed at 300 rpm for 40 min. Magnetic bar is removed and the composition is poured on top of the first gel composition layer comprising perfume composition HC-A.

After 10 hours, in a 250 mL round bottom flask, 86.15 grams of castor oil (94481, Guinama, Spain) and 13.85 grams of poly(hexamethylene diisocyanate) (418005, Sigma Aldrich) are added and mixed with a magnetic stirrer at 300 rpm for 45 minutes at 75° C. Then mixture is cooled down to 30° C., magnetic bar is removed and 5 grams of the composition is poured on top of the second gel composition layer comprising perfume composition HC-G. Then, the gel composition is taken out of the mould and is ready to be used.

After 24 hours, multilayer gel composition is ready to be used. In order to clearly distinguish the different layers, it is possible to add colorants to the different gel compositions to enhance visual effect.

Example 4: Making a Gel Composition Comprising Fragrance

In a 250 mL round bottom flask, the castor oil (94481, Guinama, Spain) and the hydrophobic composition are added and mixed at 300 rpm for 30 minutes using a magnetic stirrer at 25° C. till a homogeneous solution is formed. Then, Desmodur® eco N 7300 is added and the mixture is mixed for 30 minutes at 25° C. Magnetic bar is removed and the composition is poured into a star mould and closed to avoid fragrance evaporation during curing. After 120 hours, elastic modulus and correlation length are determined by methods described above. For the correlation length, $1/I(Q)$ is plotted vs. $Q^2$ and straight lines are fitted from $q=0.07-0.2\ \text{Å}^{-1}$. From the fitted slope and intercept, the correlation length is calculated for each sample and values are presented below. In all cases transparent gel compositions are achieved.

| Example | Hydrophobic composition | Grams castor oil | Grams hydrophobic composition | Grams cross-linker | Correlation length/nm | Elastic modulus G' (Pa) |
|---|---|---|---|---|---|---|
| 4A | Ex-F | 21   | 61 | 18   | 0.40 | 3.7 |
| 4B | Ex-F | 18.9 | 65 | 16.1 | 0.48 | 2.7 |
| 4C | Ex-H | 21   | 61 | 18   | 0.47 | 5 |
| 4D | Ex-H | 18.9 | 65 | 16.1 | 0.80 | 16 |
| 4E | Ex-A | 21   | 61 | 18   | 1.63 | 72 |
| 4F | Ex-A | 18.9 | 65 | 16.1 | 6.2  | 41 |
| 4G | Ex-C | 21   | 61 | 18   | 0.6  | 27 |
| 4H | Ex-C | 18.9 | 65 | 16.1 | 2.46 | 50 |

Example 5: Long Lasting Release

Release of gel compositions of example 4 has been measured by weight difference over time in a controlled temperature (25° C.) and humidity room (65%) and used following formula to calculate it:

$$\% \text{ Release} = \frac{\text{initial weight} - \text{weight at day } n}{\text{initial weight}} \times 100$$

wherein, initial weight is the weight in grams of the gel composition after taken the gel composition out of the mould.

n is the numbers of days that gel composition has been exposed to the air weight at day n is the weight in grams of the gel at day n

| Gel composition | % release after 10 days | % release after 30 days | % release after 60 days | % release after 90 days | Correlation length/nm | Elastic modulus G' (Pa) |
|---|---|---|---|---|---|---|
| Example 4A | 5  | 20 | 37  | 44  | 0.40 | 3.7 |
| Example 4E | 50 | 72 | n/a | n/a | 1.63 | 72 |
| Example 4G | 33 | 50 | 62  | 81  | 0.6  | 27 |

For a given polyol:cross-linker ratio, the higher the correlation length of the network the faster the release of the perfume.

Example 6

In a 250 mL round bottom flask, 18.9 grams of castor oil (94481, Guinama, Spain) and 22.7 grams of Desmodur® eco N 7300 (Covestro Germany) are added and mixed with a magnetic stirrer at 300 rpm for 40 minutes at 75° C. Then mixture is cooled down to 25° C. and 58.4 grams of perfume composition HC—H are added and mixed at 300 rpm for 50 min. Magnetic bar is removed and the composition is poured into moulds and closed to avoid fragrance evaporation during curing. Gel composition is cured after 38 hours.

Example 7

In a 250 mL round bottom flask, 18.9 grams of castor oil (94481, Guinama, Spain) and 37.8 grams of Desmodur® eco N 7300 (Covestro Germany) are added and mixed with a magnetic stirrer at 300 rpm for 40 minutes at 75° C. Then mixture is cooled down to 25° C. and 43.3 grams of perfume composition HC—H are added and mixed at 300 rpm for 50 min. Magnetic bar is removed and the composition is poured into moulds and closed to avoid fragrance evaporation during curing. Gel composition is cured after 48 hours.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A chemically cross-linked gel composition having an average correlation length of less than 8 nm as measured using Small Angle X-Ray Scattering (SAXS), wherein the gel composition comprises a hydrophobic material and a chemically cross-linked gel, wherein the chemically cross-linked gel consists essentially of a chemically cross-linked gel derived from castor oil and a cross-linking agent, and wherein the cross-linking agent is selected from the group consisting of: isocyanates, isothiocynates and mixtures thereof.

2. The gel composition according to claim 1, wherein the average correlation length is from 0.3 nm to less than 8 nm.

3. The gel composition according to claim 2, wherein the average correlation length is from 0.3 nm to about 4 nm.

4. The gel composition according to claim 1, wherein the hydrophobic material is a perfume, present at a level of from about 3 wt % to about 85 wt % of the gel composition.

5. The gel composition according to claim 4, wherein the perfume is present at a level of from about 15 wt % to about 75 wt % of the gel composition.

6. The gel composition according to claim 1, wherein the cross-linking agent is selected from the group consisting of: 1,6 hexamethylene diisocyanate (HMDI), L-Ly sine ethyl ester diisocyanate (LDI), pentamethylene diisocyanate (PDI) trimer, and mixtures thereof.

7. The gel composition according to claim 1, wherein the gel is formed using a molar ratio of castor oil to cross-linking agent of from about 1:0.75 to about 1:2.

8. The gel composition according to claim 1, wherein the hydrophobic material is a perfume or perfume mixture, and has a log P of greater than about 0.01.

9. The gel composition according to claim 8, wherein the hydrophobic material is a perfume or perfume mixture, and has a log P of greater than about 3.0.

10. The gel composition according to claim 8, wherein the hydrophobic material is a perfume or perfume mixture, and has a log P of less than about 3.

11. The gel composition according to claim 1, wherein the gel composition further comprises a hydroxyl containing polymer, a hydroxyl containing oligomer or mixtures thereof.

12. The gel composition according to claim 1, wherein the gel composition has a surface area of less than about 150 cm$^2$.

13. A multilayer composition comprising a first layer which is a gel composition according to claim 1, wherein the gel composition comprises a hydrophobic material which is a perfume, and a second layer.

14. The multilayer gel composition according to claim 13, wherein the second layer is an adhesive layer.

15. The multilayer gel composition according to claim 13, wherein the gel of the first layer is formed using a molar ratio of castor oil to cross-linking agent of from about 1:0.75 to about 1:2, and wherein the second layer comprises a gel formed using a molar ratio of castor oil to cross-linking agent of from about 1:0.05 to about 1:0.7.

* * * * *